(12) United States Patent
DiCosmo et al.

(10) Patent No.: US 6,228,393 B1
(45) Date of Patent: May 8, 2001

(54) DRUG DELIVERY VIA THERAPEUTIC HYDROGELS

(75) Inventors: Frank DiCosmo, Richmond Hill; Valerio DiTizio, North York, both of (CA)

(73) Assignee: Uroteq, Inc. (CA)

(*) Notice: Subject to any disclaimer, the term of this patent is extended or adjusted under 35 U.S.C. 154(b) by 0 days.

(21) Appl. No.: 09/412,584

(22) Filed: Oct. 5, 1999

Related U.S. Application Data

(63) Continuation of application No. 08/843,342, filed on Apr. 15, 1997, now Pat. No. 6,132,765, which is a continuation-in-part of application No. 08/631,326, filed on Apr. 12, 1996, now abandoned.

(51) Int. Cl.[7] .......................... A61K 9/127; A61M 25/00

(52) U.S. Cl. .......................... 424/450; 424/484; 424/485; 424/486; 514/82; 604/53; 604/27; 606/191; 606/194; 623/1

(58) Field of Search .................................... 424/450, 484, 424/485, 486, 487, 488; 606/191, 194; 604/27, 53; 514/82

(56) References Cited

U.S. PATENT DOCUMENTS

| | | |
|---|---|---|
| 4,442,133 | 4/1984 | Greco . |
| 4,749,585 | 6/1988 | Greco . |
| 5,575,815 | 11/1996 | Slepian . |
| 5,741,516 | 4/1998 | Webb . |

FOREIGN PATENT DOCUMENTS

| | | |
|---|---|---|
| 2181390 | 1/1997 | (CA) . |
| WO91/09616 | of 1991 | (WO) . |

OTHER PUBLICATIONS

J.W. Warren, "Management of patients in long–term care facilities with catheter–associated bacteriuria" *Infect.Urol.* 9, 147–152 (1996).

I.R. Raad and R.O. Darouchie, "Catheter–related septicemia: risk reduction." *Infect Med* 13, 807–812, 815–816, 823 (1996).

R. Nicholov, V. DiTizio, and F. DiCosmo, "Interaction of paclitaxel with phospholipid bilayers," *J. Lipo. Res.*, 5, 503–522 (1995).

M. S. Webb, T.O. Harasym, D. Masin, M. B. Bally, and L. D. Mayer, "Sphingomyelin–cholesterol liposomes significantly enhance the pharmokinetic and therapeutic properties of vincrstine in murine and human tumour models," *Br. J. Cancer*, 72, 896–904 (1995).

J. F. W. Keana and S. X. Cai, "New reagents for photoaffinity labeling and photo–lysis of functionalized perfluorphenyl azides," *J. Org. Chem.*, 55, 3640–3647 (1990).

M. J. Hope, M. B. Bally, G. Webb, and P. R. Cullis, "Production of large unilamellar vesicles by a rapid extrusion procedure. Characterization of size distribution, trapped volume and ability to maintain a membrane potential," *Biochim. Biophys. Acta*, 812, 55–65 (1985).

(List continued on next page.)

*Primary Examiner*—Gollamudi S. Kishore
(74) *Attorney, Agent, or Firm*—Burns, Doane, Swecker & Mathis, L.L.P.

(57) ABSTRACT

The present invention is directed to a vehicle for effecting drug delivery from a solid substrate. Hydrogels loaded with liposomal therapeutic agents such as antibiotics are covalently bonded to the surface of substrates such as in-dwelling medical devices, such as implants, catheters, and the like. The present invention is particularly useful in the treatment and prevention of biofilm mediated infection often associated with the use of in-dwelling medical devices.

25 Claims, 5 Drawing Sheets

PEG-Gelatin Hydrogel with Antibiotic Containing Liposomes

OTHER PUBLICATIONS

Figure 1:
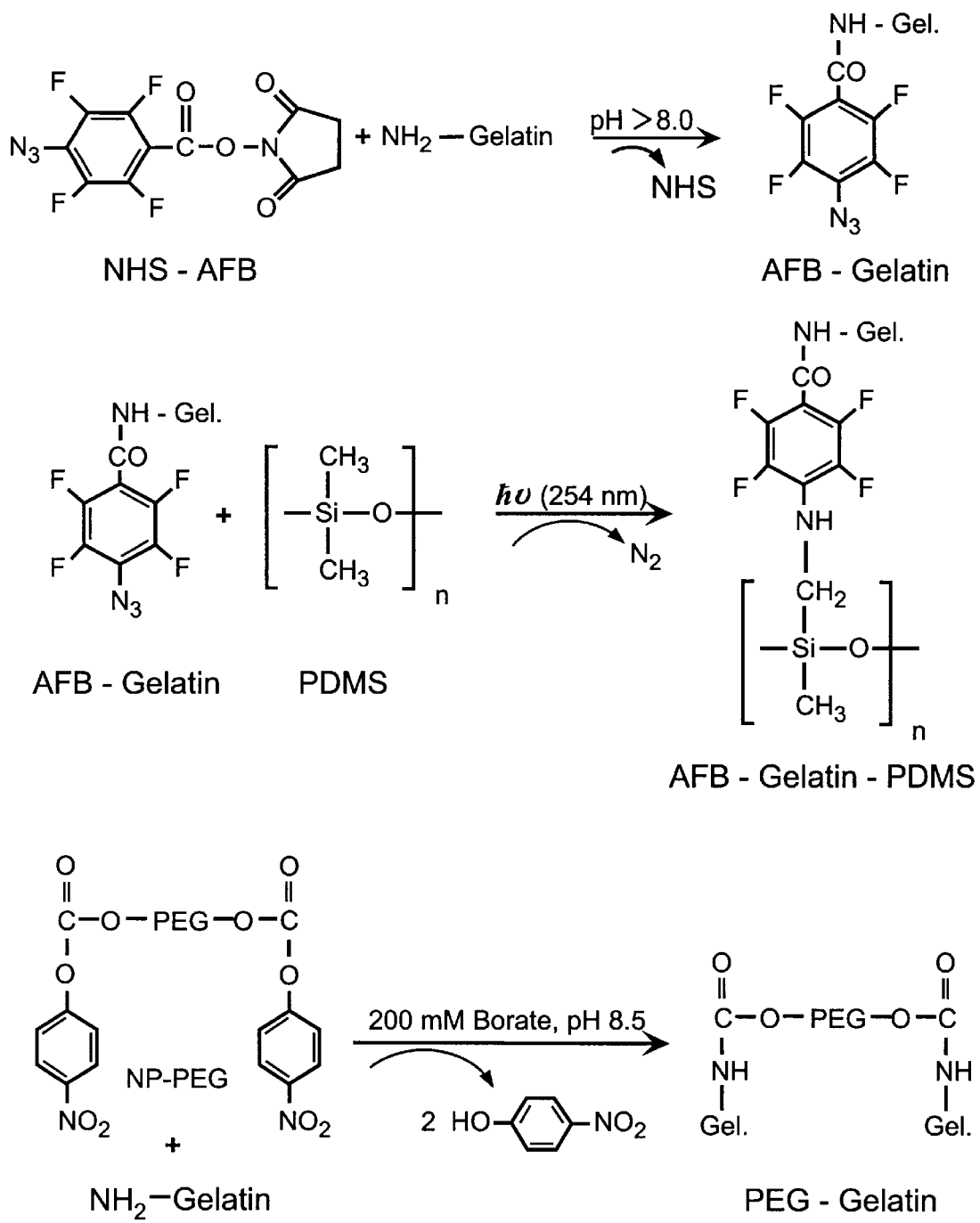
Figure 3:
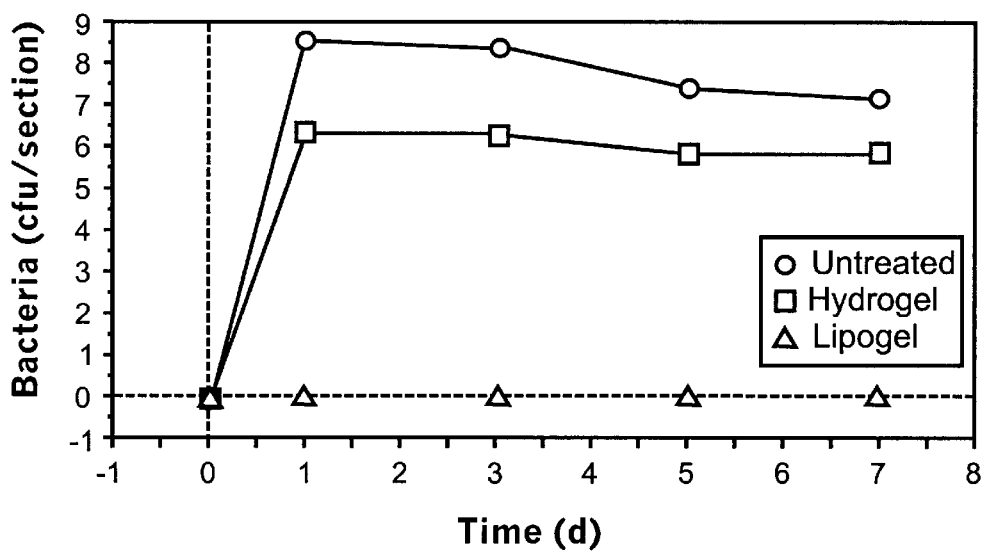

L. D. Mayer, M. J. Hope, P. R. Cullis, and A. S. Janoff, "Solute distributions and trapping efficiencies observed in freeze–thawed multilamellar vesicles," *Biochim. Biophys. Acta,* 817, 193–196 (1986).

Y.–K. Oh, D. E. Nix, and R. M. Straubinger, "Formulation and efficacy of liposome–encapsulated antibiotics for therapy of intracellular *Mycobacterium avium* infection," *Antimicrob. Agents Chemother.,* 39, 2104–2111 (1995).

A. K. Shrock and G. B. Schuster, "Photochemistry of phenyl azide: chemical properties of the transient intermediates," *J. Am. Chem. Soc.,* 106, 5228–5234 (1984).

E. Leyva, M. J. T. Young, and M. S. Platz, "High yields of formal CH insertion products in the reactions of polyfluorinated aromatic nitrenes," *J. Am. Chem. Soc.,* 108, 8307–8309 (1986).

L. M. Crowe, J. H. Crowe, A. Rudolph, C. Womersley, and L. Appel, "Preservation of freeze–dried liposomes by trehalose," *Arch. Biochem. Biophys.,* 242, 240–247 (1985).

W. Q. Sun, A. C. Leopold, L. M. Crowe, J. H. Crowe, "Stability of dry liposomes in sugar glasses," *Biophys. J.,* 70, 1769–1776 (1996).

J. E. Eastoe and A. A. Leach, "Chemical constitution of gelatin," in *Science and Technology of Gelatin,* A. G. Ward and A. Courts (eds.), Academic Press, New York, 1977, pp. 73–107.

J. N. Nacey and B. Delahunt, "Toxicity study of first and second generation hydrogel–coated latex urinary catheters," *Br. J. Urol.,* 67, 314–316 (1991).

T. Okada and Y. Ikada, "In vitro and in vivo digestion of collagen covalently immobilized onto the silicone surface," *J. Biomed. Mater. Res.,* 26, 1569–1581 (1992).

Y. Kinoshita, T. Kuzuhara, M. Kirigakubo, M. Kobayashi, K. Shimura, and Y. Ikada, "Soft tissue reaction to collagen–immobilized porous polyethylene: subcutaneous implantation in rats for 20 wk," *Biomaterials,* 14, 241–247 (1993).

T. Okada and Y. Ikada, "Tissue reactions to subcutaneously implanted, surface–modified silicones," *J. Biomed. Mater. Res.,* 27, 1059–1518 (1993).

Y. Aldenhoff et al., "Studies on a New Strategy for Surface Modification of Polymeric Biomaterials," *Journal of Biomedical Materials Research,* (1995) 29:917–928.

T. Sugawara et al., "Synthesis of Phenylazido–derivatized Substances and Photochemical Surface Modification to Immobilize Functional Groups," *Journal of Biomedical Materials Research,* (1996) 32:157–164.

Z. Wachol–Drewek et al., "Comparative Investigation of Drug Delivery of Collagen Implants Saturated in Antibiotic Solutions and a Sponge Containing Gentamicin," *Biomaterials* (1996) 17:1733–1738, No. 17.

J. Schierholz et al., "In–vitro Efficacy of an Antibiotic Releasing Silicone Ventricle Catheter to Prevent Shunt Infection," *Biomaterials* (1994) 15:996–1000, No. 12.

A. Oloffs et al., "Biocompatibility of Silver–Coated Polyurethane Catheters and Silver–Coated Dacron® Material," *Biomaterials* (1994) 15:753–758, No. 10.

D. Stickler et al., "Bacterial Biofilm Growth on Ciprofloxacin treated urethral Catheters," *Cells and Materials* (1994) 4:387–398, No. 4.

N. Hasaniya et al., "Efficacy of Subcutaneous Silver–Impregnated Cuffs in Preventing Central Venous Catheter Infections," *Chest* (1996) 109:1030–32.

D. Ciresi et al., "Failure of Antiseptic Bonding to Prevent Central Venous catheter–Related Infection and Sepsis," *The American Surgeon* (1996) 62:641–646, No. 8.

Y. Nakayama et al., "Surface Fixation of Hydrogels Heparin and Glucose Oxidase Hydrogelated Surfaces," *ASAIO Journal* (1992) M421–M424.

H. Sigrist et al. "Surface Immobilization of Biomolecules by Light," *Optical Engineering* (1995) 34:2339–2347, No. 8.

T. Matsuda et al., "Novel Photoreactive Surface Modification Technology for Fabricated Devices," *Trans Am Soc Artif Intern Organs* (1990) M161–M164.

T. Okada et al., "Surface Modification of Silicone for Tissue Adhesion," *Biomaterials and Clinical Applications,* (1987) 465–470.

K. Matsuda et al., "Evaluation of a Bilayer Artificial Skin Capable of Sustained Release of an Antibiotic," *Biomaterials* (1992) 13:119–122, No. 2.

E. Trafny et al., "Anti–Pseudomonal Activity of Collagen Sponge with Liposomal Polymyxin B," *Pharmacological Research* (1996) 33:63–65, No. 1.

A. Weiner et al., "Liposome–Collagen Gel Matrix: A Novel Sustained Drug Delivery System," *Journal of Pharmaceutical Sciences* (1985) 74:922–925.

L. Mikulec et al., "Use of p–nitrophenyl Chloroformate Chemistry to Immobilize Protein on Orthopedic Biomaterials," *Journal of Biomedical Materials Research* (1996) 32:203–208.

M.W. Mittelman et al., "Liposomal–Hydrogel Delivery of Ciprofloxacinat Catheter Surfaces", 37th Interscience Conference on Antimicrobial Agents and Chemotherapy, Toronto, Canada, Sep. 28–Oct. 1, 1997, Abstracts 37 (0) p. 325.

M.J. Swanson and G.W. Opperman, "Photochemical Surface Modification of Polymers for Improved Adhesion," *J. Adhesion Sci. Technol.* 9:385–391 (1995).

Weiner, "Liposome–Collagen Gel Matrix: A novel Sustained Drug Delivery System" *J. Pharm. Sciences* 74:922 No. 9 (Sep. 1985).

Reaction schemes for the (a) binding of AFB to gelatin, (b) the attachment of AFB-gelatin to a silicone catheter surface, and (c) the cross-linking of gelatin by NP-PEG.

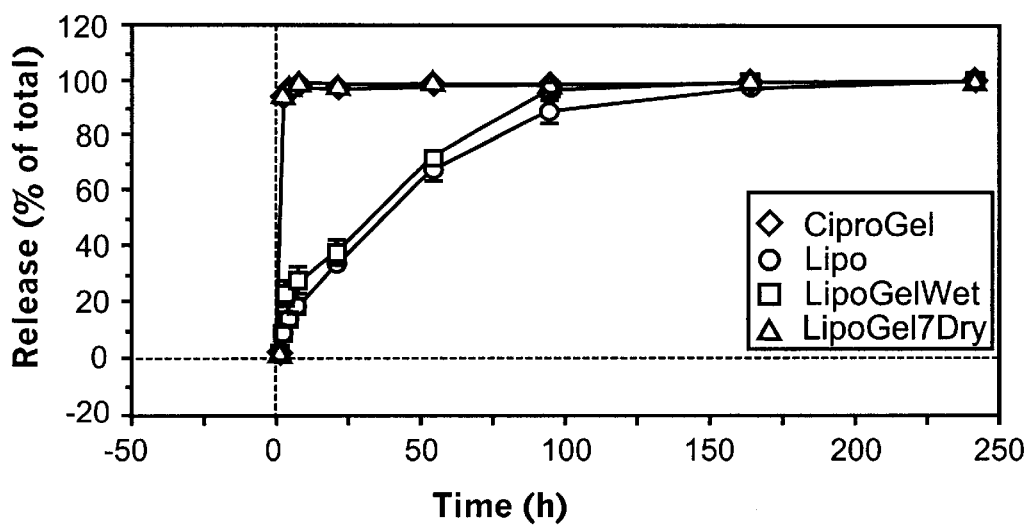

The release of ciprofloxacin from catheter sections coated with PEG-gelatin hydrogels expressed as a percentage of the total amount released. The treatments consisted of constantly hydrated hydrogels loaded with ciprofloxacin alone (◊) or with liposomal ciprofloxacin (□), and pre-dried hydrogels containing liposomal ciprofloxacin (Δ). The release of ciprofloxacin from liposomes alone was also determined (O).

Figure 2

The adherence of viable bacterial to catheter sections coated with PEG-gelatin hydrogel (□), sections treated with PEG-gelatin hydrogel containing liposomal ciprofloxacin (△), and untreated sections (○).

DRUG DELIVERY VIA THERAPEUTIC HYDROGELS

CROSS REFERENCE TO RELATED APPLICATIONS

This application is a continuation of application Ser. No. 08/843,342, filed Apr. 15, 1997 now U.S. Pat. No. 6,132,765, which is a Continuation-in-Part of application Ser. No. 08/631,326, filed Apr. 12, 1996 now abandoned.

FIELD OF THE INVENTION

The present invention is directed to an effective drug delivery vehicle involving the containment of a therapeutic agent within a hydrogel, which hydrogel is then bound to a substrate. The substrates of the present invention include any in-dwelling medical device or implant, wound dressings, wound closures, and the like. The present invention further provides means for compounding such hydrogels and affixing such hydrogels to a substrate.

BACKGROUND OF THE INVENTION

The control of infection acquired in a clinical setting is a major and significant health care problem. Infections contracted during patient treatment within healthcare facilities have been estimated to contribute to ninety-thousand (90,000) deaths and cost $12 Billion dollars U.S. to treat per annum.

Nosocomial bacteriuria is the most common infection contracted in long-term care facilities and is usually associated with catheterization. The condition is virtually universal in patients after thirty days of catheterization. Complications will include fever, acute and chronic pyelonephritis, bacteremia and renal stones. The extralumenal surface of the catheter may become colonized with bacteria and act as a conduit for bacterial entry into the bladder. The best preventative measure is to limit the use of long-term in-dwelling catheters; this is often not possible. J. W. Warren, "Management of patients in long-term care facilities with catheter-associated bacteriuria" *Infect. Urol.* 9, 147–152 (1996). However, all patients will develop bacteriuria if catheterized for a long enough period.

Catheter-related septicemia occurs in approximately 400,000 of the estimated five million Americans who are catheterized each year. Treatment for a single event of catheter-related septicemia in a critically ill patient adds approximately 6.5 days to a stay in an intensive care unit and will cost about $29,000. I. R. Raad and R. O. Darouchie, "Catheter-related septicemia: risk reduction." *Infect Med* 13:807–812, 815–816, 823 (1996). Indeed, catheter-related septicemia represents the most common life-threatening complication associated with intravascular catheters. There is a strong relationship between catheter-site inflammation and the recovery of bacteria from the surface of the device. In situ, the catheter surface becomes colonized with opportunistic microbial pathogens, and these colonies become the source of infections.

A common source for catheter colonization and catheter-related sepsis is the skin insertion site. Indeed, the skin surface is the most common source of short-term catheter colonization and subsequent infection. Catheter-related infections remain a significant problem in healthcare facilities. It is generally accepted that no method has yet emerged for the adequate and satisfactory management of catheter-related infection.

The adhesion of microorganisms to the catheter surface is related to the interaction of the host, the microorganisms and the catheter material. The host tissue reacts to the catheter material as a foreign body and deposits a thrombin coat over the material, which becomes colonized with microbes, often within 24 hours; this coating of protein and microorganisms is called a biofilm. In the biofilm, microbes find a suitable niche for continued growth as well as for protection from antibiotics, phagocytic neutrophils, macrophages and antibodies.

There have been numerous attempts to produce biomedical products that impede or prevent infection. Biomedical products that incorporate and release silver compounds for infection control have been studied for many years. However, clinical studies of these products, including catheters, have shown only minor improvements in infection control. The devices have been described to exhibit resistance to infection, but in practical application fail to adequately inhibit infection.

Ciresi et al. 1996 (*Am Surg* 62:641–646) compared the incidence of catheter-related infection and catheter-related sepsis between a standard catheter and the recently released Arrowgard™ catheter in a clinical trial with one-hundred-ninety-one patients receiving total parenteral nutrition. The Arrowgard™ catheter contains a combination of silver sulfadiazine and chlorhexidine, that is thought to render the catheter surface resistant to bacterial colonization and subsequent sepsis. The authors concluded that the coating of the central venous catheters with sulfadiazine and chlorhexidine does not reduce the rate of catheter-related infection or catheter-sepsis when compared with a standard central venous catheter in patients receiving total parenteral nutrition.

Hasaniya et al. 1996 (*Chest* 109:1030–1032) found that the use of an attachable subcutaneous silver-impregnated cuff failed to decrease the incidence of central venous catheter-related infection and sepsis.

In U.S. Pat. No. 4,442,133 there is disclosed a process for vascular prostheses with a cationic surfactant, e.g. tridodecylmethyl-ammonium chloride (TDMAC), to increase sites for antibiotic bonding. Before the prostheses are used they are dipped or coated in a solution of TDMAC to adsorb the antibiotic.

Stickler et al. 1994 (*Cells and Materials* 4:387–398), conclude that pretreatment by adventitious coating of catheters with ciprofloxacin (an antibiotic) is unlikely to prevent bacterial biofilm formation on long-term, in-dwelling silicone or silicone-coated latex urethral catheters.

U.S. Pat. No. 4,749,585 provides a method for coating a prosthesis with an ionically charged surfactant and an antibiotic compound encapsulated within phospholipid vesicles, wherein said vesicles have a surface charge opposite to that of said surfactant. The drawback of this system is that the amount of liposomes coated on to the surface is generally low, not allowing for a therapeutic dose of drug to be retained on the device for periods of time necessary to suppress or alleviate the infection. Second, upon insertion of a device, such as a catheter so treated, it is expected that the surface coating of ionically bound liposomes will be sheared off from the area where the liposomes were intended to reside.

Oloffs et al. 1994; *Biomaterials* 15:753–758, describe the biocompatibility of silver-coated polyurethane catheters and silver coated Dacron® material to inhibit infection. These fail to inhibit catheter-related bacterial infection at the infection site (vide supra).

Schierholz, J. et al. 1994; *Biomaterials* 15:996–1000, disclose the incorporation of antibiotic into an antibiotic releasing silicone ventricle catheter to prevent shunt infection. The antibiotic (rifampicin) was added to the swelling-activated polydimethylsiloxane matrix and would diffuse from the matrix.

Wachol-Drewek et al. 1996, *Biomaterials* 17:1733–1738, disclose the use of collagen implants of various structures and a gelatin sponge which were placed in antibiotic solutions and allowed to absorb the compounds. They concluded: "If an implant that has a protective effect against wound infections over a period of 24–48 h is required, the materials described here are suitable. However, where treatment in infected areas should ensure antibiotic cover for 5–10 d[days] neither collagen materials immersed in antibiotics nor collagen sponges containing gentamicin are suitable."

Several studies have used photoactivated surface modification in attempts to improve the biocompatibility of biomedical devices. The synthesis of phenylazido-derivatized substances and photochemical surface immobilization of functional groups is presented by Sugawara & Matsuda (*J Biomed Mater Res* 32:157–164).

The surface modification of silicone by corona discharge for the immobilization of various proteins is disclosed by Okada et al. 1987 (*Biomaterials and Clinical Applications*, pp. 465–470, Pizzoferrato, A., Marchetti, P. G., Ravglioli, A., & Lee, A.J.C. Elsevier Scientific Publishers, Amsterdam).

Photoreactive surface modification of fabricated devices is described in Matsuda & Inoue 1990 (Trans Am Soc Artif Intern Organs, Poster Session 1, *Biomaterials*, pp. M161–M164). Nakayama & Matsuda 1992 (*ASAIO Journal* 38:M421–424) describe the incorporation of heparin, useful as a thromboresistant molecule, within a hydrophilic co-polymer of poly(N,N-dimethylacrylamide)-poly(2-cinnamoylethyl methacrylate) linked to a polyethylene terephthalate surface using a photochemical process; poly (m-azidostyrene) was initially applied to the polyethylene terephalate surface to provide a reactive interface. The procedure produces a cross-linked matrix in which heparin is retained. Sigrist et al. (*Optical Eng.* (1995) 34:2339–2347) describe surface immobilization of biomolecules by light. Aldenhoff & Koole (*J Biomed. Mate. Res.* (1995) 29:917–928) describe a method for the photoimmobilization of protein to polyurethane surfaces.

The clinical problem remains that the catheter-related biofilm mediated infection can only be adequately treated by surgical intervention and removal of the bacterial-laden device followed with antibiotic therapy, and surgical re-insertion of a new medical device at a later date. The discomfort to patients and the high costs of these procedures are evident.

The treatment of biofilm-mediated infection on the surface of medical devices is currently extremely difficult, and no medical device or remedy presently available adequately manages liquid-flow conduit line-related infection. Therefore, there is an urgent need for a method of providing adequate doses of antibiotic consistently in targeted fashion on the surface of in-dwelling medical devices so that bacteria are unable to establish a biofilm during the first five to ten, or more days after insertion of the medical device or application of dressings, suture, pins, clips, and other medical devices. There remains a need to develop a practical method for deterring microbial biofilm development on the surface of catheters and other in-dwelling medical devices in contact with tissue, so that device-related infections are significantly reduced.

It is an object of the present invention to provide a biocompatible hydrogel matrix, containing liposomal antibiotic that can be coated onto the surface of in-dwelling biomedical devices. It is a further objective to provide methods for formulating such hydrogel matrix compositions; and it is a still further objective to provide methods to co-valently attach said hydrogel to the surface of substrates such as catheters. The type of drug incorporated into the hydrogel formulation is not restricted to any single antibiotic, or combination of one or more of these. Similarly, the hydrogel composition might comprise a variety of active agents including antibiotics, hormones, growth factors and other factors that are beneficial for the condition under management, in accordance with sound medical judgement.

SUMMARY OF THE INVENTION

The present invention avails the use of antibiotic-loaded liposomes sequestered within a biocompatible hydrogel retained on the surface of the biomedical device, e.g. catheter. Liposomes, microspheres, nanospheres, biodegradable polymers, and other systems are excellent drug delivery vehicles; and the methods of preparation and drug loading procedures for liposomes and the others are well-known in the art. Liposomes can store both apolar and polar compounds via interactions with the biocompatible and biodegradable lipid bilayer, or compartmentation within the aqueous core, respectively.

A method for producing a biofilm-resistant surface might involve the binding of antibiotic-containing liposomes directly to the surface. Theoretical calculations however, indicate that if a surface was saturated with drug-carrying liposomes, only about 150 ng of the antibiotic ciprofloxacin could be localized per square centimeter of surface. Nanogram quantities of ciprofloxacin are unlikely to provide protection from microbes over substantial periods of time, e.g. several days or more. We have devised a means to effectively exploit the space above the catheter's surface to significantly increase the surface area concentration of bound liposomal antibiotic. Specific formulation of the liposome bilayer allows for drug release over a period ranging from days to weeks. See, e.g., R. Nicholov, V. DiTizio, and F. DiCosmo, "Interaction of paclitaxel with phospholipid bilayers," *J. Lipo. Res.,* 5, 503–522 (1995). M. S. Webb, T. O. Harasym, D. Masin, M. B. Bally, and L. D. Mayer, "Sphingomyelin-cholesterol liposomes significantly enhance the pharmokinetic and therapeutic properties of vincristine in murine and human tumour models," *Br. J Cancer,* 72, 896–904 (1995). Furthermore, the biocompatibility of liposomes ensures that they will be safely degraded and assimilated by the host after their supply of drug is exhausted after six days or more.

The method of the present invention provides for co-valently attaching liposomes to a substrate such as a catheter, or other liquid-flow conduit, or other device, such as a wound dressing. The method exploits the surface area of the device as well as the volume occupied by the hydrogel matrix bonded to the surface. The volume of gel matrix can accommodate large quantities of drug-loaded liposomes, microspheres, nanospheres, or other drug carrier and consequently, relatively high doses of a therapeutic drug can be deposited at specific sites. The hydrogel matrix is biocompatible and biodegradable (i.e. does not release potentially toxic degradation products), and will ensure protection of the liposomes from membrane-disrupting shear forces that are encountered during handling and insertion of the device, and from rapid degradation of the liposome in vivo. The containment of the liposomes within the gel matrix also creates an opportunity to control drug diffusion rates, thereby affording long-term drug efflux.

Thus, the present invention includes a method for loading efficacious quantities of a liposomal therapeutic agent on a medical device by mixing said liposomal therapeutic agent with a hydrogel, and covalently binding said hydrogel to a pre-formed polymeric surface of a medical device. By pre-formed polymeric surface is meant that the polymeric material used in fabricating the medical device is formed or manufactured in advance of the covalent attachment of the hydrogel. As discussed more fully below, covalent attachment of the hydrogel to the polymeric material can be effected through the use of a bifunctional linker molecule, preferably one comprising an azide functional group. Preferably, the pre-formed polymeric surface is a silicone rubber.

One such embodiment is a silicone catheter loaded with a co-valently bonded polyethylene glycol-gelatin matrix containing a liposomal antibiotic-carrier coating to control catheter-related infections, such as bacteriuria and septicemia. Medical devices where the coating can be used include catheters, wound closures, surgical dressings, temporary orthopedic implants and others.

The liposomal hydrogel of the present invention includes a variety of hydrogel drug combinations. Generally, the selection or pairing of the hydrogel and drug is determined only by the desired application and relevant indication. That is, any active agent that can be compounded into liposomes, microspheres, nanospheres, or other suitable encapsulation vehicle can be confined within the hydrogel matrices of the present invention to create the therapeutic hydrogels of the present invention. Those hydrogels can then be affixed to a substrate such as the surface of a catheter or other in-dwelling liquid conduit, or the substrate or matrix of a wound closure or wound dressing material.

One embodiment of the present invention involves the deposition and co-valent attachment of a polyethylene glycol-gelatin matrix layer to the surface of in-dwelling biomedical implants (e.g. catheters, stents, intravenous tubes, dialysis tubes, orthopedic implants, surgical sponges and wound dressings, etc.) and the sequestration or co-valent attachment of liposomes to the constituents of the matrix. The liposomes contain a therapeutic. The matrix thus constitutes a vehicle for the containment of high concentrations of therapeutic agent such as one or more antibiotics, hormones, steroids, growth factors, antihistamines, colony stimulating factors, interleukins, and the like, and/or combinations thereof. The therapeutic hydrogels of the present invention can be used in the management of tissue and biomaterial associated infection. The matrix can be a hydrogel (e.g., gelatin, pectin, etc.), a protein (e.g. collagen, hemoglobin, etc.), or other adjuvant. Preferably, the matrix will have some structural integrity as by cross-linking or similar structural support to impart resistance to shear forces resulting from insertion of the device.

Thus, the present invention provides a medical device having a polymeric substrate; a matrix material covalently bound to said substrate; and a liposomal therapeutic agent confined within said matrix material. The matrix material can be a hydrogel, a protein, or other suitable adjuvant. The matrix material will preferably be a cross-linked material. One example is gelatin cross-linked with polyethylene glycol as by reacting gelatin with bis-(amine)-PEG.

Matrix material can be covalently bound to a substrate by a variety of means. For example, a protein such as gelatin can be derivatized with a bifunctional linker molecule such as 4-azido-2,3,5,6-tetrafluorobenzoic acid. That is, the carbonyl carbon of the benzoic acid group can be made to react with a free amine of a protein to form an amide; the azido functionality can be made to react with a methylene carbon of the silicone rubber. In this manner, the matrix material is covalently bonded to the substrate.

The therapeutic hydrogels of the present invention serve as support material for a variety of liposomal therapeutics. Any therapeutic agent suitable for encapsulation in a liposome, microsphere, nanosphere or the like can be utilized in the present invention. For example, therapeutic agents useful in the present invention include antibiotics, antihistamines, hormones, steroids, therapeutic proteins, and the like.

It will be appreciated by those of ordinary skill in the art that the desired concentration of active agent within a hydrogel loaded on a substrate will vary depending upon the characteristics of the chosen active agent. For example, as between an antibiotic and a therapeutic protein, the required concentration of antibiotic, which are generally active in the microgram range, will likely be higher than the concentration of a therapeutic protein, many of which are active in the nanogram range. Other standard dosing criteria will also be considered in selecting the concentration ranges of active agent loaded onto the substrate in accordance with standard practice in the art.

A preferred embodiment of the present invention is a gelatin hydrogel cross-linked with polyethylene glycol (PEG); and dispersed within the hydrogel is a liposomal antibiotic such as ciprofloxacin. Ciprofloxacin has been shown to exhibit good activity against a broad spectrum of bacteria, particularly those associated with urinary tract infections.

Such embodiments provide dramatically improved in-dwelling medical devices. Medical devices of the present invention can be loaded with as much as 1000 $\mu g/cm^2$ ciprofloxacin. Preferred embodiments have about 10–300 $\mu g/cm^2$; and still more preferred embodiments have about 25–200 $gg/cm^2$. Thus, the present invention avails long-term, slow release of an anti-infective active agent from an in-dwelling medical device; and dramatically reduces the frequency with which such in-dwelling medical devices must be removed and replaced.

The PEG-gelatin-liposome mixture can be effectively applied to the surface of a silicone Foley catheter that has been pre-treated with phenylazido-modified gelatin. Methods for immobilization of photoreactive gelatin on the catheter's surface are presented herein. Use of silicone devices is not a limiting feature, as any such polymeric device can be treated to harbor a hydrogel in which liposomes, or other drug carriers are sequestered.

More specifically, the present invention provides a method for associating substantial quantities of antibiotic-releasing liposomes with a silicone Foley catheter through their inclusion in a surface-coating of PEG-gelatin hydrogel covalently linked to the silicone surface, and the antibiotic was released to the surrounding area over a period of greater than five days. Modifications of the technique should allow it to be applied to other medical devices as well, such as, intraperitoneal catheters, joint and vascular prostheses, and reconstructive implants. An attractive feature of this system is the possibility of sustained release of compounds having a range of chemical properties, such as antibiotics, enzymes, growth factors, human hormones, anticoagulants, etc. Also, the surface characteristics of the PEG-gelatin hydrogel will improve biocompatibility of the device as hydrogel-coated catheters tend to minimize the inflammation associated with the presence of any foreign object in the body. J. N. Nacey and B. Delahunt, "Toxicity study of first and second generation hydrogel-coated latex urinary catheters," Br. J. Urol., 67:314–316 (1991). The inclusion of gelatin in our hydrogel system will lead to its eventual degradation in vivo leaving a co-valently-bonded surface layer of AFB-gelatin that should be relatively resistant to further protease digestion. T. Okada and Y. Ikada, "In vitro and in vivo digestion of collagen covalently immobilized onto the silicone surface," *J. Biomed Mater. Res.*, 26:1569–1581 (1992). It is possible that the remaining layers of gelatin will facilitate better integration of the catheter with the surrounding tissue.

The liposomal matrix materials of the present invention can be used to prevent or treat patients at risk of or suffering from biofilm mediated infection or other forms of infection associated with in-dwelling medical devices, wound closures, and the like. The method comprises inserting into a patient a medical device of the present invention, said medical device comprising a substrate, as for example, a silicone rubber substrate, and covalently bound to said substrate is a hydrogel within which is dispersed a liposomal therapeutic material such as an antibiotic. Likewise, the method comprises replacing infected medical devices with the medical devices of the present invention.

Definitions

By hydrogel or gel is meant any material forming, to various degrees, a jelly-like product when suspended in a solvent, typically water or polar solvents. These gels can be proteins such as collagen or hemoglobin, or more conventional hydrogels such as gelatin, pectin, and fractions and derivatives thereof.

By liposomal therapeutic agents is meant any physical structure surrounding or encapsulating a therapeutic agent such as a drug. Thus, liposomal therapeutic agents will include various drugs or biologically active agents such as antibiotics, antihistamines, hormones, steroids, growth factors, colony stimulating factors, interleukins, and the like confined or encapsulated within a structure such as a liposome, whether of unilamellar or bilayer structure, or microspheres or nanospheres or the like.

A bifunctional linker molecule is any molecule possessed of at least two functional groups that can chemically react with and form covalent bonds with other functional groups or chemical substituents such as the free amines of proteins and the like. Preferably, the bifunctional linker will have an aryl amine functionality, as in an aroyl azide group, and a carbonyl functionality, as in a carboxylic acid group.

BRIEF DESCRIPTION OF THE DRAWINGS

FIG. 1 illustrates a reaction scheme for binding AFB to gelatin, the attachment of AFB-gelatin to a silicone catheter surface, and the cross linking of gelatin by NP-PEG.

FIG. 2 is a graphical representation of the release of ciprofloxacin from catheter sections coated with PEG-gelatin hydrogels over time.

FIG. 3 illustrates a comparison of the adherence of viable bacteria (expressed as exponents to power of 10) to catheter sectins coated with (a) PEG-gelatin hydrogel, (b) catheter sections coated with PEG-gelatin hydrogel containing liposomal ciprofloxacin (lipogel), and (c) untreated sections.

FIG. 4 illustrates the reaction scheme whereby the cross linked PEG-gelatin matrix is formed by the formation of amide bonds between bis-(amine)-PEG and the free carboxyl groups of gelatin.

FIG. 5 schematically illustrates the PEG-gelatin hydrogel with antibiotic containing liposomes.

DETAILED DESCRIPTION OF THE INVENTION

AFB-Gelatin Preparation and Degree of Substitution

NHS-AFB was prepared as described in J. F. W. Keana and S. X. Cai, "New reagents for photoaffinity labeling and photolysis of functionalized perfluorophenyl azides," *J. Org. Chem.*, 55:3640–3647 (1990) using the coupling agent DCC. AFB-gelatin of varying degrees of substitution was synthesized by the addition of NHS-AFB in methanol to a solution of gelatin (0.5–1.0%) in 50 mM Borate buffer (pH 8.6). The mixture was incubated overnight at room temperature with stirring. Following filtration through 0.22 $\mu$m Millex-GS syringe filters (Millipore, Bedford, Mass.), the solution was dialyzed for 24 hours at 4° C. with three changes of water (pH=4.6 when dialysis complete). The benzoylated gelatin precipitated under these conditions and was collected by centrifugation (10,000×g for 10 minutes). The precipitate was dried in vacuo for 2 hours. All procedures involving AFB were performed in the dark or under dim light conditions.

The degree to which gelatin's amino groups reacted with NHS-AFB was determined. In brief, 20 $\mu$g of gelatin or AFB-gelatin in 1.5 mL of 50 mM $Na_2PO_4$ buffer (pH 8.0) was used. While mixing the protein solution using a vortex agitator, 0.5 mL of fluorescamine in dioxane (1.1 mM) was added and mixing continued for 15 seconds. The fluorescence intensity at 475 nm was measured (390 nm excitation wavelength and 8 nm slit widths) and used to calculate the degree of substitution, α, according to the equation $\alpha=F_p-F_s/(F_p+0.078\cdot F_s)$, where $F_p$=fluorescence of gelatin, $F_s$=fluorescence of AFB-modified gelatin, and $0.078\cdot F_s$ represents a correction factor accounting for the increase in molecular weight of gelatin completely substituted with AFB.

Determination of the Amount of Gelatin Bound to Silicone Surface

Gelatin was iodinated using Iodo Beads (Pierce, Rockford, Ill.) according to the supplier's directions. In brief, 100 $\mu$g of gelatin (500 $\mu$L of 0.2 mg/mL gelatin in Hepes buffered saline, pH 7.4 (HBS)) was added to a vial containing 4 Iodo Beads in 2 mL of HBS. $Na^{125}I$ (1 mCi from Amersham Canada, Oakville, ON) was added to the reaction vial and left to react for 15 minutes. Transfer of the protein to a second vial terminated the reaction. The reaction vial was washed with three 0.5 mL aliquots (200 $\mu$g/mL) of unlabeled gelatin. The protein solution (approx. 400 $\mu$g in 2.1 mL of HBS) was dialyzed in 200 mL of buffer until the dialysate was minimally radioactive (approx. 48 hrs with 5 changes of medium).

The specific activity of the iodinated gelatin was determined by a technique that exploits the insolubility of the complex formed between gelatin and the dye Sirius Red in acetic acid Four 50 $\mu$L aliquots were removed from the iodinated protein solution and added to 1.5 mL polypropylene centrifuge tubes, followed by the addition of 50 $\mu$L of HBS and 1 mL of Sirius Red (50 $\mu$M) in 0.5 M acetic acid. The tubes were incubated at room temperature for 30 minutes and subsequently centrifuged at 12,000×g for 30 minutes. The supernatant was removed and a portion (0.5 mL) was used for protein quantitation via the decrease in absorbance (540 nm) of the dye remaining in solution. The protein/dye pellet was resuspended with three 150 $\mu$L washes of 0.2 N NaOH containing 2 mg/mL gelatin. The radioactivity of the eluate was measured in a liquid scintillation counter. Control experiments indicated that the presence of Sirius Red in the scintillation fluid did not interfere with the determination of $^{125}I$ radioactivity. Residual adsorbed protein was measured by cutting the centrifuge tubes into quarters and placing them in scintillation vials for counting. The specific activity was calculated to be 0.12±0.01 $\mu$Ci/$\mu$g. This level of labeling is consistent with the paucity of tyrosine and histidine residues in gelatin.

Photoimmobilization Efficiency of AFB-($^{125}$I)gelatin

Radioiodinated gelatin was modified with AFB as described above, however, the coupling solution and dialysis medium consisted of HBS (pH 8.0 and 7.4, respectively). The ratio of NHS-AFB to gelatin in the coupling solution was 1:4 (w/w). Following dialysis, the volume of the AFB-($^{125}$I)gelatin solution was made up to 5 mL and the protein concentration was determined to be 3.9±0.6 ng/$\mu$L. Aliquots (10 $\mu$L each) of radioiodinated AFB-gelatin were applied to the side of silicone rectangles corresponding to the outer surface of the original catheter. All sections (12 in total) were dried under vacuum for 90 minutes. One set of four catheter pieces were then immediately placed in scintillation fluid (exterior surface facing up) for counting. Another set was exposed to short wave (254 nm) UV light (Minerallight Lamp, UVP, San Gabriel, Calif.) at a distance of 2 cm for 3 minutes. This set of four sections plus the remaining four sections were subsequently washed in 1% SDS solution at 80° C. for 30 minutes with a change of medium after 15 minutes. The sections were rinsed in distilled water and placed in scintillation vials for counting.

Liposome and PEG-gelatin Gel Preparation

Liposomes were composed of DPPC/Cholesterol/PEG-DSPE/Rhodamine-DPPE in a 1:1:0.05:0.001 ratio. The formulation to be used is not limiting, and any number of lipid-to-other-constituents ratios may be used to effectively achieve the embodiments of this invention. The lipids were dissolved in 4 mL of chloroform and the solvent was removed in vacuo. The resulting lipid film was placed under vacuum for two hours and subsequently hydrated with 1 mL of 250 mM ammonium sulfate (pH 2.5) at 45° C. Liposomes were then frozen in liquid nitrogen and thawed in a 45° C. water bath (5×), followed by high-pressure extrusion through two 100 nm-pore membranes (10×X). This procedure has been shown to produce unilamellar liposomes with an average diameter of 100 nm and an equal solute distribution between the exterior and interior of the liposomal membrane. M. J. Hope, M. B. Bally, G. Webb, and P. R. Cullis, "Production of large unilamellar vesicles by a rapid extrusion procedure. Characterization of size distribution, trapped volume and ability to maintain a membrane potential," *Biochim. Biophys. Acta*, 812:55–65 (1985); L. D. Mayer, M. J. Hope, P. R. Cullis, and A. S. Janoff, "Solute distributions and trapping efficiencies observed in freeze-thawed multilamellar vesicles," *Biochim. Biophys. Acta*, 817:193–196 (1986). External ammonium sulfate was removed by passing the suspension through a G-50 column (1×10 cm) and eluting with a 10% sucrose solution (pH 4.0).

PEG-gelatin solutions consisted of 10% gelatin, 6% NP-PEG and 10% sucrose at pH 4.0. If liposomes were required, they were added from a pure liposome suspension. The concentration of liposomes in PEG-gelatin solutions was 15 mM with respect to DPPC. All solutions were heated at 45° C. for 15 min. to dissolve gelatin.

Crosslinking the Gelatin Matrix

Figure 4:
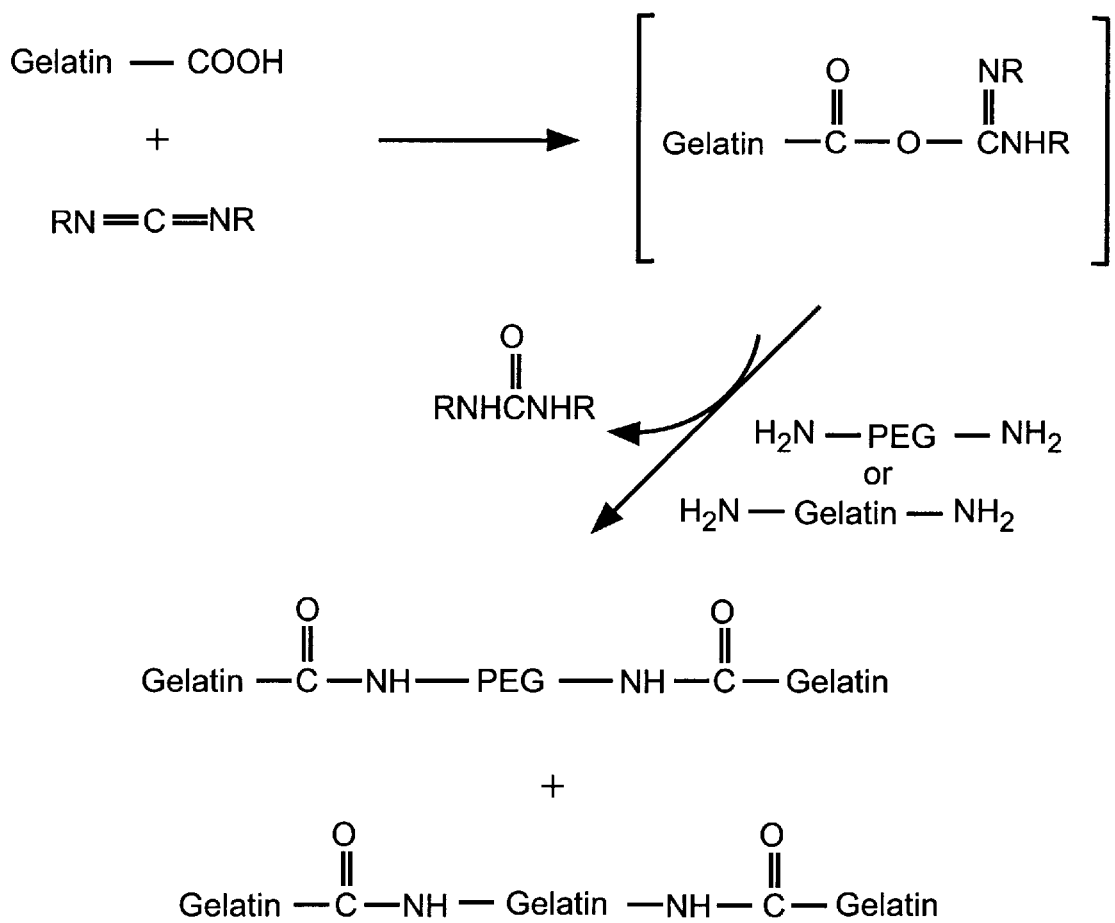
Figure 5:
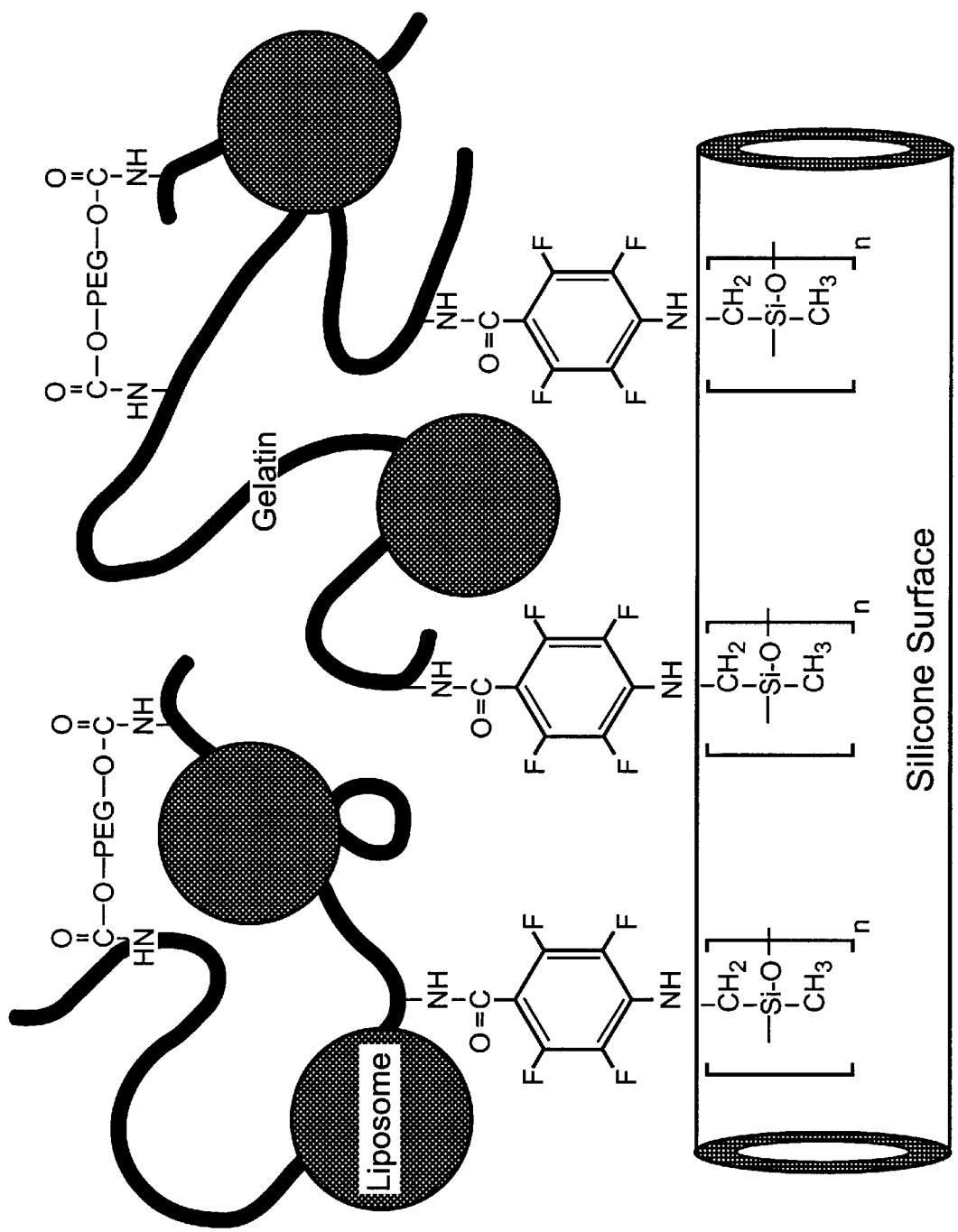

The PEG-gelatin matrix was also crosslinked by the formation of amide bonds between bis-(amine)-PEG and the free carboxyl groups of gelatin. In this method, the silicone catheter surface is immersed in a solution of aqueous soluble carbodiimide (2 mg/mL) and incubated at room temperature for 30 min. The reaction of the activated carboxyl groups with PEG and gelatin amino moieties is initiated by submersing the silicone material in borate buffer (200 mM, pH 8.5). Incubation in the alkaline buffer proceeds for 2 hr. Subsequently, the silicone surface is placed in 10% sucrose solution for 6 hr, with three changes of medium, to remove non-crosslinked material. This treatment results in a crosslinked PEG-gelatin gel that retains its integrity and remains affixed to the catheter for at least seven days when placed in a 37° C. solution of 10% sucrose. The crosslinking chemistry is outlined in FIG. 4.

Preparation of Catheter Sections

In the preferred embodiment of the invention catheter material that is to be coated with PEG-gelatin gel is first spin-coated with 10 $\mu$L of AFB-gelatin (5 mg/mL; $\alpha$=55%) and dried under vacuum for 1 hour. All sections, including untreated controls, were exposed to UV light (254 nm) for 3 minutes and rinsed with water. Subsequently, catheter pieces are spin-coated with 60 $\mu$L of fluid PEG-Gelatin or PEG-gelatin-liposome mixture and incubated at 4° C. for 15 minutes. Incubation may occur at temperatures from 4–10° C. Gels were polymerized by submersing catheter sections in 200 mM Borate buffer (pH 8.5) for 1 hr. Residual p-nitrophenol was leached from the gels by incubation at room temperature in 10% sucrose (pH 4.0) for 12 hrs, with four changes of medium. The absence of p-nitrophenol was confined by negligible absorbance of the dialysate at 410 nm.

Liposomes in suspension and those entrapped within PEG-gelatin gels were loaded with ciprofloxacin (Bayer, Leverkusen, Germany) according to the remote-loading technique described in Y. K. Oh, D. E. Nix, and R. M. Straubinger, "Formulation and efficacy of liposome-encapsulated antibiotics for therapy of intracellular *Mycobacterium avium* infection," *Antimicrob. Agents Chemother.*, 39:2104–2111 (1995). Catheter pieces were placed in 10% sucrose solution (pH 7.5) containing 2 mM ciprofloxacin, while for liposomes in suspension, an appropriate amount of drug was added to make the suspension 2 mM in ciprofloxacin. Incubation in both cases proceeded for 1 hour at 45° C. The liposome suspension was centrifuged at 3000×g for 5 minutes to pellet drug crystals and the supernatant was then applied to a G-50 column (1×10 cm) to remove unentrapped ciprofloxacin.

Dehydrated hydrogels were prepared by drying coated catheter sections in an oven at 35° C. for 2.5 hr. The dried gels were then rehydrated in Tris buffer (10 mM Tris, 110 mM NaCl, pH 7.4) or in concentrated ciprofloxacin-HCl solution (25 mg/mL) as required. The temperature during the rehydration process was maintained at 45° C.

TABLE I

Ciprofloxacin Loading into Liposomes and PEG-Gelatin Gel

| Sample | Total Ciprofloxacin Entrapped |
| --- | --- |
| PEG-Gelatin Gel[a] | 42 ± 12 $\mu$g/cm$^2$ |
| PEG-Gelatin-liposome Gel[a] | 185 ± 16 $\mu$g/cm$^2$ |
| PEG-Gelatin-Liposome Gel[b] | 3083 ± 267 $\mu$g/cm$^3$ |
| Dry PEG-Gelatin-Liposome Gel[a] | 173 ± 6 $\mu$g/cm$^2$ |
| Dry PEG-Gelatin Gel[a,c] | 1253 ± 80 $\mu$g/cm$^2$ |
| Dry PEG-Gelatin-Liposome Gel[a,c] | 1298 ± $\mu$g/cm$^2$ |
| Liposomes-only | 0.52 ± 0.04 $\mu$mol cipro/$\mu$mol lipid |

[a]Based on the application of 60 $\mu$L of PEG (6%)-Gelatin (10%) gel to a 1 cm segment of silicon catheter with a diameter of 0.3 cm. Liposome-containing gels were 15 mM in dipalmitoyl-phosphatidylcholine, n = 4.
[b]Since 1 cm$^3$ = 1 mL, 1000 $\mu$L of gel would occupy 1 cm$^3$ and this quantity of PEG-Gelatin-Liposome gel would sequester 185 ± 16 $\mu$g * (1000 $\mu$L/60 $\mu$L) = 3083 ± 267 $\mu$g of ciprofloxacin.
[c]These samples were dried before being rehydrated in a concentrated ciprofloxacin solution (25 mg/mL).

The quantity of therapeutic agent loaded on the substrate can be increased or decreased over greater ranges than those shown in Table I. Greater concentrations of therapeutic agent can be loaded by increasing the amount of drug encapsulated and mixed into the hydrogel. For example, we expect that concentrations up to about 1,000 $\mu$g (1.0 mg) per cm$^2$ or more of an antibiotic active agent can be loaded on substrates with the methods of the present invention; and that concentrations of up to about 10,000 $\mu g/cm^3$ or more can be loaded on substrates. A preferred concentration range of antibiotic loaded on such substrates is about 10–1,000 $\mu g/cm^2$. A preferred range for ciprofloxacin is about 10–200 $\mu g/cm^2$.

Similarly, quantities of therapeutic agent can be increased by increasing the quantity of gel immobilized on the surface of the substrate. Generally, hydrogel layers of about 0.5–10 mm thick can be loaded on substrates to effect the desired drug delivery and therapeutic results; preferred layers are in the range of about 1–5 mm; and especially preferred layers are about 2–4 mm.

Thus, one of skill in the art will appreciate that the present methods and devices afford highly versatile means for loading high concentrations of anti-infective agents, and of varying the concentration of such agents, on a substrate or on a specific area of a substrate.

Determination of Drug Efflux Kinetics

The release experiment was initiated by placing each catheter section or dialysis membrane (containing liposome suspension 2.7 mM in DPPC) into separate liquid scintillation vials filled with 15 mL of Tris buffer. At selected time intervals 3 mL was removed from each vial for ciprofloxacin quantitation via a fluorescence-based assay using an excitation wavelength of 324 nm, an emission wavelength of 450 nm, and 5 nm slit widths. The amount of ciprofloxacin present was determined by comparisons to a standard curve. The remaining solution in the vials was emptied and replaced with 15 mL of buffer. The samples were incubated at 37° C. throughout the experiment.

Bacterial Biofilm Formation Assay

A clinical isolate of *Pseudomonas aeruginosa* obtained from a patient with peritonitis was used for all challenge assays. An 18 h nutrient broth culture was prepared from a primary isolate maintained at −70° C. in a 50% (v/v) glycerol-phosphate buffered saline (PBS) solution.

Catheter sections were aseptically placed in 100 mL of sterile nutrient broth (Difco, Detroit, Mich.) contained within a 250 mL glass beaker. Twelve catheter sections from each coating formulation were added to individual beakers. The *P. aeruginosa* culture was washed 3 times in a pH 7.1 PBS solution, then inoculated to each of the beakers. The inoculum size was sufficient to yield $1.5 \pm 0.5 \times 10^7$ cfu/mL in the 100 mL volume. The inoculated catheter suspensions were then placed in an incubator maintained at 37° C. and agitated at a rate of 100 rpm. One half of the 100 mL volume was aseptically removed from each beaker and replaced with a like volume of sterile nutrient broth on a daily basis. At time intervals of 1, 3, 5, and 7 days, triplicate catheter sections were removed from each of the beakers and viable bacteria were recovered from the catheter surfaces as described below. The number of viable bacteria in nutrient broth samples was also determined.

The catheter sections were removed from the bacterial suspensions and individually rinsed with a 10 mL volume of sterile PBS delivered via a gravity feed from a 10 mL pipet. The rinsed sections were placed in 20 mL plastic test tubes containing 5 mL volumes of sterile PBS and 3 mm diameter glass beads. Following sonication for 30 s in an ice cold sonicator bath (Bransonic, Danbury, Conn.), the catheter sections were vortexed for 1 minute at high speed. The sonication and vortexing procedure was repeated three times. Aliquots were then removed from each of the suspensions and plated to nutrient agar. The plates were incubated at 37° C. for 48 h.

Degree of Substitution of AFB-gelatin

The modification of the silicone catheter surface in this example used the photoreactive molecule 4-azido-2,3,5,6-tetrafluorobenzoic acid (AFB). It can be linked to the amino groups of gelatin via N-hydroxysuccinimide (NHS) chemistry. Based on the amino acid composition of ox hide gelatin, (J. E. Eastoe and A. A. Leach, "Chemical constitution of gelatin," in *Science and Technology of Gelatin*, A. G. Ward and A. Courts (eds.), Academic Press, New York, 1977, pp. 73–107) the typical gelatin molecule (MW 75,000) contains approximately 25 $\epsilon$-amino groups derived from lysine and hydroxylysine. The reactivity of these groups towards NHS-AFB was determined by varying the ratio of gelatin to NHS-AFB. Table 1 shows that a 1:9 ratio of $\epsilon$-amino groups to NHS-AFB leads to nearly complete (99%) substitution of available amino groups. A 1:0.75 ratio results in approximately 55% substitution. Fifty-five percent substitution represents the optimal value for the modification of gelatin with AFB because it allows for both binding to the surface via the azide moiety and attachment to the PEG-gelatin coating through linkage to the carbonate group of NP-PEG. However, lower or higher substitutions can be used to achieve a desired effect.

Binding of AFB-gelatin to Silicone

The high reactivity of aryl azides has been exploited in biochemistry for some time via the use of photoaffinity ligands. Such azides typically yield poor carbon-hydrogen (C—H) insertion efficiencies due to competing side reactions exemplified by ring expansion. A. K. Shrock and G. B. Schuster, "Photochemistry of phenyl azide: chemical properties of the transient intermediates," *J. Am. Chem. Soc.*, 106:5228-(1984). Fluorination of the benzene ring promotes excited state stability and results in improved insertion efficiencies. E. Leyva, M. J. T. Young, and M. S. Platz, "High yields of formal CH insertion products in the reactions of polyfluorinated aromatic nitrenes," *J. Am. Chem. Soc.*, 108:8307 (1986). The fluorinated aryl azide (AFB) used for the present invention has been shown to be capable of binding to various atoms in usually inert chemical groups such as the carbon in methyl groups. A possible reaction scheme for AFB-gelatin linkage to polydimethylsiloxane (PDMS) via C—H insertion is depicted in FIG. 1B.

To date no data has been published regarding the ability of AFB to insert into a PDMS-based (silicone rubber) network.

In order to verify that AFB-gelatin covalently attaches to the surface of a silicone catheter, a small volume of a dilute solution of radioiodinated AFB-gelatin was placed onto sections of catheter, dried under vacuum, exposed to UV light, and vigorously washed in detergent solution at high temperature. The radioactivity measured in samples exposed to UV light minus the radioactivity detected in the unexposed samples was taken as a measure of the amount of gelatin that was covalently bound to the silicone. It was found that UV irradiated samples bound approximately 32 times more AFB-gelatin than did unirradiated samples (approximately 5.1 ng versus 0.16 ng). An estimation of the binding efficiency was obtained from division of the radioactivity detected in UV exposed samples by the radioactivity measured in samples that had been placed in scintillation fluid immediately after the initial drying step. The binding efficiency was measured as 27±5%. This value is an approximately upper limit since the AFB-gelatin used had an $\alpha$ value of 93%. The data suggest that AFB-gelatin forms covalent links to the silicone catheter's surface.

Ciprofloxacin Efflux Studies

Ciprofloxacin release rates were determined for the following samples: liposomes-only, PEG-gelatin hydrogel alone, a liposomal PEG-gelatin hydrogel, and a drug-containing liposomal hydrogel that was air dried and then rehydrated with pH 7.4 Tris buffer. All the liposomes used in this study contained DPPC and cholesterol. PEG-lipid was also included to avoid gelatin-induced destabilization of the bilayer and to increase immobilization of the liposomes within the hydrogel matrix via stearic interactions. The results of the experiment are summarized in FIG. 2. The quantity of ciprofloxacin released at a given time point is expressed as a percentage of the total amount released throughout the experiment. There are two notable trends. The hydrogel-only, and rehydrated liposomal hydrogel treatments were not successful in retaining ciprofloxacin for a sustained period of time; almost all of the drug initially incorporated was released within the first two hours.

Surprisingly, it took longer than 6.8 days (or 163 hrs) for greater than 99% of the initially incorporated drug to be released from liposomes and the liposomal hydrogel that was not dehydrated. The similarity in results for the latter two treatments indicates that hydrogel-embedded liposomes maintain their integrity during the coating procedure and throughout the experimental period. It should be noted that all hydrogels remained affixed to the catheter surface for at least seven days. This is a practical solution in delivering antibiotic or other drug to the site of infection or other tissue area in need of treatment, respectively, for a time greater than five or more days.

Also, the presence of rhodamine-DPPE in the membrane of liposomes endowed liposomal hydrogels with a pink color that did not noticeably decrease in intensity throughout the course of the experiment indicating that the liposomes remained embedded within the hydrogel and did not shift from the intended locations.

The dried liposomal hydrogel, i.e., dried prior to being loaded with antibiotic, was found to maintain its sustained release properties after rehydration and is an important consideration for the clinical application of the system. An effective drying and rehydration process uses the dried liposomal hydrogel rehydrated in a solution containing 25 mg of ciprofloxacin. As a control, a dried hydrogel containing no liposomes was hydrated in a 25 mg/mL ciprofloxacin solution. The total average amount of antibiotic entrapped within these hydrogels is listed in Table 2, and for comparative purposes the total entrapped drug is also included. The hydrogels rehydrated in concentrated ciprofloxacin solution (25 mg/mL) retained very large quantities of antibiotic (approx. 1.4 mg/1 cm catheter section). Almost all (>99%) of the hydrogel-associated ciprofloxacin was released after the first four hours of incubation, as expected from an analysis of the prior art.

The release kinetics of ciprofloxacin from selected hydrogel treatments can be followed by analyzing the data in Table 3. Despite the large initial release of antibiotic, it is evident that there was still a small, but continual release of ciprofloxacin from the dried liposomal hydrogels rehydrated in concentrated ciprofloxacin solution. In comparison, the release of ciprofloxacin from the dried hydrogel-only treatment was negligible from 20.5 hours and onwards.

Ciprofloxacin was incorporated into dried liposomal hydrogels during the rehydration step since our data indicated that pre-loaded liposomes embedded in a hydrogel were destabilized by dehydration. In effect, antibiotic was encapsulated within liposomes as they reformed during the rehydration of the PEG-gelatin film. Our calculations indicate that the encapsulation efficiency of ciprofloxacin in liposomes generated in situ was 7% relative to the amount of ciprofloxacin in pre-formed liposomes. The variation can be accounted for by the different loading techniques used. In general, compounds are more efficiently concentrated within liposomes when using a remote-loading technique exploiting pH and ammonium sulfate gradients than when a lipid film hydration method is employed.

The optimal efflux profile in terms of prolonged release of substantial antibiotic quantities was obtained from liposomal hydrogel samples that were not dehydrated. The hydrogel system was shown to be capable of releasing substantial quantities of drug for up to 7 days. It is possible to improve the amount and duration of release by increasing the concentration of liposomes within the hydrogel; this aspect is not limiting. For example, the concentration can be at least doubled without affecting hydrogel stability. Increasing the liposome concentration allows the air dried liposomal hydrogel system to become a viable alternative as this compensates for the decrease in drug encapsulation efficiency associated with the in situ generation of liposomes. Alternatively, a dried liposomal hydrogel with suitable sustained release properties as presented here may be obtained by the development of a lyophilization protocol. Numerous studies have shown that liposomes freeze-dried in the presence of sugars such as sucrose or trehalose can be rehydrated without substantial loss of their contents. L. M. Crowe, J. H. Crowe, A. Rudolph, C. Womersley, and L. Appel, "Preservation of freeze-dried liposomes by trehalose," *Arch. Biochem. Biophys.*, 242:240–247 (1985); W. Q. Sun, A. C. Leopold, L. M. Crowe, J. H. Crowe, "Stability of dry liposomes in sugar glasses," *Biophys. J.*, 70:1769–1776 (1996).

Bacterial Biofilm Formation Assay

A practical aim of this invention is toward a catheter, or any polymeric biomedical device coating capable of resisting colonization by bacteria and subsequent infection in vivo and during application. To this end, untreated, PEG-gelatin coated, and ciprofloxacin-containing liposomal hydrogel catheter sections were challenged with a clinical strain of *P. aeruginosa* known to form biofilms on silicone catheters. The hydrogel coating containing antibiotic liposomes was effective in preventing cells from adhering and remaining viable. The number of viable bacteria in the broth containing these sections was approximately $6.7 \times 10^2$ cfu/mL at the end of the experiment. This suggests that the absence of viable cells on the catheter surface was not simply due to the total elimination of the initial inoculum resulting from the release of drug during the first few hours. It is likely that the continual release of ciprofloxacin for a time greater than five days significantly contributed to the nearly complete prevention of adhesion of viable bacteria and elimination of the potential biofilm. Another contributing factor may have been the presence of PEG in the hydrogel. Previous studies have shown that polymers coated with polyoxyethylene chains can prevent or retard bacterial cell adhesion. Fewer bacteria were able to adhere to catheter sections coated with PEG-gelatin gel relative to untreated samples. The approximately two order of magnitude decrease in bacterial cell adhesion may be further improved by increasing the concentration of PEG in the hydrogel.

General

The phospholipids dipalmitoylphosphatidylcholine (DPPC) and PEG-distearoylphosphatidylethanolamine (PEG-DSPE) were obtained from Avanti Polar Lipids (Alabaster, Ala.). Rhodamine dipalmitoylphosphatidylethanolamine (rhodamine-DPPE) and 4-azido-2,3,5,6-tetrafluorobenzoic acid (AFB) were purchased from Molecular Probes (Eugene, Oreg.). Porcine gelatin-a (MW 50,000–100,000), polyoxyethylene bis(p-nitrophenyl carbonate) (NP-PEG), and cholesterol were obtained from Sigma (St. Louis, Mo.). Fluorescamine, 1,3-dicyclohexylcarbodiimide (DCC), N-hydroxysuccinimide (NHS), and Sirius Red were purchased from Aldrich (Milwaukee, Wis.). All reagents and solvents were of analytical grade and were used without further purification. Deionized water (Milli-Q, Millipore, Bedford, Mass.) filtered through a 0.22 µm membrane was used in all experiments. Ciprofloxacin (Bayer, Germany) was analyzed in a Perkin Elmer LS-50 fluorimeter. Sirius Red and p-nitrophenol were quantitated using a Hewlett-Packard 8450 spectrophotometer.

Silicone Foley catheters (Sherwood Medical, St. Louis, Mo.) were prepared for use by sectioning into cylinders (3 mm diameter and 10 mm length). The open ends of the sections were sealed with silicone rubber (RTV 108, GE, Pickering, ON). Occasionally, cylindrical sections were further subdivided into rectangular pieces (5 mm×3 mm). Silicone sections were cleaned prior to each experiment by refluxing in methanol for six hours.

Two pediatric silicone Foley catheters were coated with a PEG-gelatin-liposome composition of the present invention as described herein, under aseptic conditions. The catheters were inserted into the urethra of two male New Zealand white rabbits. After ten minutes the catheters were removed; and the catheters and excised urethra were examined. No disruption of the gel was observed on the catheter, and no gel fragments were detected in the urethra.

Table 2. The degree of substitution of gelatin with AFB as a function of the initial ratio of a ε-amino groups to NHS-AFB.

| ε-NH$_2$/NHS-AFB | Degree of Substitution (%) |
|---|---|
| 9 | 99 ± 4 |
| 2 | 93 ± 4 |
| 1 | 71 ± 5 |
| 0.75 | 55 ± 2 |

Table 3. Release of ciprofloxacin from liposomes alone, constantly hydrated liposomal PEG-Gelatin hydrogel (LipoGel), dried liposomal PEG-Gelatin gel rehydrated 25 mg/mL ciprofloxacin solution (DryLipoGel (25 mg)), and dried PEG-Gelatin gel rehydrated in 25 mg/mL ciprofloxacin solution (DryGel (25 mg)).

| TIME (Hours) | CIPROFLOXACIN RELEASED (µg/15 mL) | | | |
|---|---|---|---|---|
| | Liposomes | LipoGel | DryLipoGel (25 mg) | DryGel (25 mg) |
| 2.0 | 6.1 ± 2.1 | 39.5 ± 9.2 | 1367 ± 52 | 1329 ± 86 |
| 4.0 | 3.0 ± 0.4 | 7.3 ± 2.1 | 22.5 ± 4.8 | 22.0 ± 1.9 |
| 7.5 | 3.3 ± 0.5 | 7.2 ± 1.0 | 3.8 ± 0.9 | 1.2 ± 0.3 |
| 20.5 | 10.1 ± 0.6 | 21.6 ± 2.1 | 3.5 ± 0.3 | 0.34 ± 0.11 |
| 53.5 | 23.2 ± 4.0 | 67.7 ± 5.7 | 2.5 ± 0.2 | 0.14 ± 0.02 |
| 93.5 | 14.8 ± 4.1 | 47.7 ± 2.4 | 1.4 ± 0.2 | 0.13 ± 0.04 |
| 163.0 | 5.6 ± 0.9 | 7.4 ± 0.5 | 1.1 ± 0.1 | 0.15 ± 0.09 |

What is claimed is:

1. A medical device comprising:
    a. a stent having a polymeric external surface;
    b. a gelatin hydrogel matrix material; and
    c. a therapeutic agent encapsulated in a liposome and confined within said matrix material, wherein said gelatin hydrogel matrix material is affixed to the polymeric surface of said stent by a plurality of covalent bonds.

2. The medical device of claim 1, wherein the gelatin hydrogel matrix material is cross-linked with polyethylene glycol.

3. The medical device of claim 1, wherein the polymeric surface on said stent comprises silicone rubber.

4. The medical device of claim 3, wherein the silicone rubber comprises polydimethylsiloxane.

5. The medical device of claim 3, wherein the hydrogel matrix material is a polyethylene glycol-gelatin matrix.

6. The medical device of claim 3, comprising a bifunctional linker molecule covalently linked to an amine functionality of said gelatin and covalently linked to a methylene functionality of said silicone rubber.

7. The medical device of claim 6, wherein said linker molecule is a 4-azido-2,3,5,6-tetrafluorobenzoyl radical.

8. The medical device of claim 1, wherein the liposomal therapeutic agent is selected from the group consisting of: antibiotics, antihistamines, anti-inflammatories, hormones, steroids, growth factors, colony stimulating factors, interleukins, and combinations thereof.

9. The medical device of claim 1, wherein the liposomal therapeutic agent is an antibiotic.

10. The medical device of claim 1, wherein the liposomal therapeutic agent is a fluoroquinolone antibiotic.

11. The medical device of claim 10, wherein the fluoroquinolone antibiotic is selected from the group consisting of: ciprofloxacin, norfloxacin, ofloxacin, pefloxacin, enoxacin, rosoxacin, amifloxacin, fleroxacin, temafloxacin, and lomefloxacin.

12. The medical device of claim 10, wherein the fluoroquinolone is ciprofloxacin.

13. The medical device of claim 1, wherein the liposomes are formed of a material selected from the group consisting of dipalmitoylphosphatidylcholine and polyethyleneglycol-distearoylphosphatidylethanolamine.

14. A medical device comprising:
    a. a stent having a silicone rubber external surface;
    b. a bifunctional linker molecule comprising a fluorinated aroyl azido group covalently bound to said external surface of said stent;
    c. a layer of a polyethylene glycol-gelatin matrix material affixed to the external surface of said stent by a covalent bond between an amine functionality of said gelatin and said bifunctional linker molecule; and
    d. liposomal ciprofloxacin dispersed throughout said matrix material.

15. A medical device comprising a stent having a silicone rubber external surface to which is affixed a therapeutic hydrogel comprised of a mixture of gelatin and therapeutic agent encapsulated in a liposome such that the external surface of the stent is loaded with about 10–1,000 µg therapeutic agent per cm$^2$.

16. The medical device of claim 15, wherein the therapeutic agent is ciprofloxacin.

17. A medical device comprising a stent having a silicone rubber external surface having a plurality of covalent bonds with an internal surface of a layer of a therapeutic hydrogel comprised of a mixture of gelatin and therapeutic agent encapsulated in a liposome such that an external surface of said conduit is loaded with about 50–200 µg ciprofloxacin per cm$^2$.

18. A method for the prophylaxis or treatment of patients at risk of or suffering from biofilm mediated infection associated with the use of an in-dwelling medical device comprising inserting or applying a stent having a external polymeric surface, said external polymeric surface having a plurality of covalent bonds connecting said substrate with a surface of a layer of a gelatin-based therapeutic hydrogel matrix comprised of a mixture of gelatin and therapeutic agent encapsulated in a liposome.

19. The method of claim 18, wherein said therapeutic hydrogel matrix comprises a liposomal fluoroquinolone antibiotic dispersed throughout said matrix.

20. The method of claim 19, wherein said fluoroquinolone antibiotic is ciprofloxacin.

21. The method of claim 18, wherein said polymeric substrate is a silicone rubber.

22. The method of claim 18, wherein said hydrogel is a polyethylene glycol-gelatin matrix.

23. A method for the prophylaxis or treatment of patients at risk of or suffering from biofilm mediated infection associated with the use of an in-dwelling medical device comprising inserting a stent having an external silicone rubber surface having a plurality of covalent bonds with a surface layer of polyethylene glycol-gelatin matrix material, and wherein dispersed within said matrix material is a fluoroquinolone antibiotic encapsulated in a liposome.

24. The method of claim 23, wherein said fluoroquinolone is ciprofloxacin.

25. The medical device of claim 1 wherein the plurality of covalent bonds between the polymeric surface of said stent and said gelatin hydrogel matrix material further comprises a linker molecule covalently bound between said external surface of said catheter and said layer of said gelatin hydrogel matrix material.

* * * * *